United States Patent
Chung et al.

(10) Patent No.: US 9,328,123 B2
(45) Date of Patent: May 3, 2016

(54) ROTENONE DERIVATIVES AND A USE THEREOF

(71) Applicant: Korea Atomic Energy Research Institute, Daejeon (KR)

(72) Inventors: Byung Yeoup Chung, Gochang-eup (KR); Tae Hoon Kim, Daegu (KR); Seung Sik Lee, Jeongeup-si (KR); Hyoungwoo Bai, Jeongeup-si (KR); Sungbeom Lee, Jeongeup-si (KR); Chul Hong Park, Daegu (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 14/693,795

(22) Filed: Apr. 22, 2015

(65) Prior Publication Data
US 2015/0225416 A1    Aug. 13, 2015

Related U.S. Application Data

(63) Continuation-in-part of application No. PCT/KR2013/008487, filed on Sep. 23, 2013.

(30) Foreign Application Priority Data

Oct. 24, 2012 (KR) .................. 10-2012-0118392

(51) Int. Cl.
| | |
|---|---|
| *C07D 493/22* | (2006.01) |
| *A61K 31/537* | (2006.01) |
| *C07D 493/14* | (2006.01) |
| *C07D 493/20* | (2006.01) |
| *B01J 19/08* | (2006.01) |

(52) U.S. Cl.
CPC ............ *C07D 493/22* (2013.01); *A61K 31/537* (2013.01); *B01J 19/08* (2013.01); *C07D 493/14* (2013.01); *C07D 493/20* (2013.01)

(58) Field of Classification Search
CPC ............................ A61K 31/537; C07D 493/22
USPC .......................................... 549/382; 514/453
See application file for complete search history.

(56) References Cited

FOREIGN PATENT DOCUMENTS

WO    2007 137135    11/2007
WO    WO 2007/137135    * 11/2007

OTHER PUBLICATIONS

Chen et al. (Journal of Photochemistry and Photobiology B: Biology 95 (2009) 93-100).*
Ahmad-Junan et al. (1992) "Novel and Efficient Synthesis of Rotenoids via Intramolecular Radical Arylation," J. Chem. Soc. Perkin Trans. pp. 1:539-545.
Liu et al. (2012) "Design, Synthesis and Cytotoxic Activity of Novel Spin-Labeled Rotenone Derivatives," Bioorganic & Medicinal Chemistry Letters 22:920-923.
Snyder et al. (1999) "(−)-6', 7'-[$^{11}$C]Dihydroroten-12α-ol ((−)-[$^{11}$C]DHROL) for In Vivo Measurement of Mitochondrial Complex I," Journal of Labelled Compounds and Radiopharmaceuticals 42(7):641:652.
International Search Report for PCT/KR2013/008487, Feb. 3, 2014.

* cited by examiner

*Primary Examiner* — Valerie Rodriguez-Garcia
(74) *Attorney, Agent, or Firm* — Lathrop & Gage LLP

(57) ABSTRACT

The present invention relates to rotenone derivatives and a use of the same. Particularly, the present inventors identified rotenoisin A and B which are compounds with no toxicity and which are prepared by irradiation with gamma rays onto rotenone as represented by the following formula 1. It was further confirmed that the rotenone derivatives significantly inhibited pancreatic lipase activity and preadipocyte differentiation. The rotenone derivatives of the present invention can be effectively used as a composition for the prevention and treatment of obesity and as a composition for health functional food for the prevention and improvement of obesity:

[Formula 1]

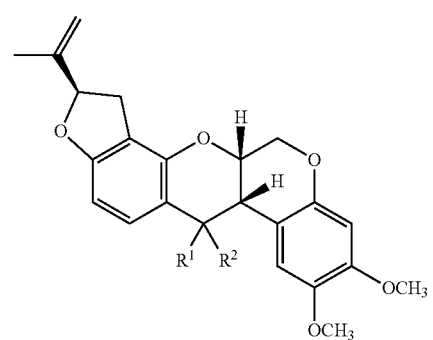

(In formula 1, $R^1$ and $R^2$ are as defined in this description).

2 Claims, 1 Drawing Sheet

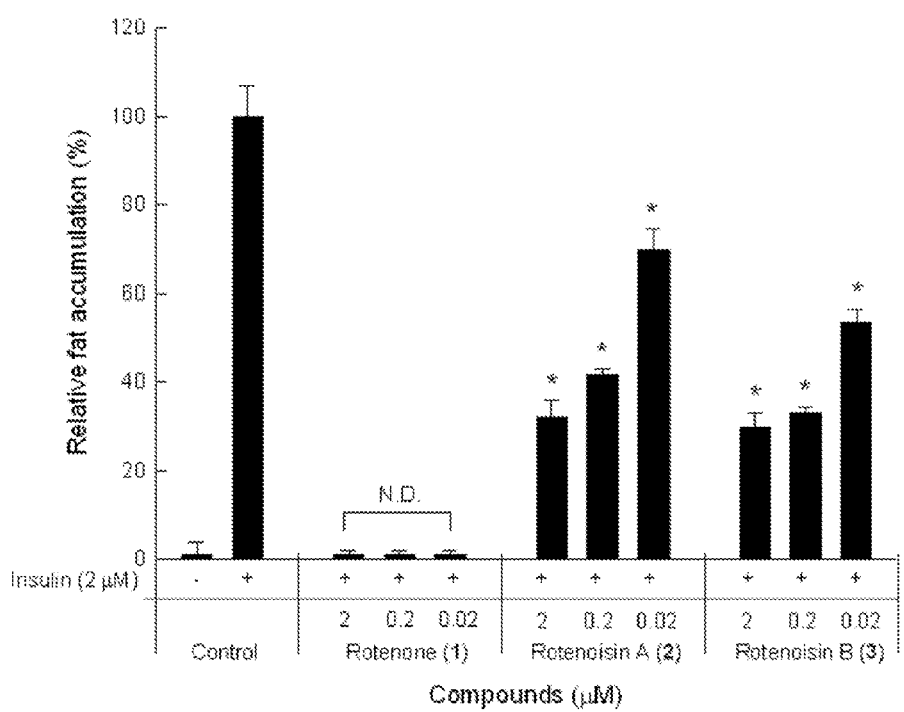

ROTENONE DERIVATIVES AND A USE THEREOF

CROSS-REFERENCE TO RELATED APPLICATIONS

This application is a continuation-in-part application which claims the benefit of International Application No. PCT/KR2013/008487, filed on Sep. 23, 2013, and published on May 1, 2014 as WO 2014/065510, which claims priority to South Korean Application No. 10-2012-0118392, filed on Oct. 24, 2012, all of which are incorporated by reference in their entireties.

TECHNICAL FIELD

The present invention relates to the novel rotenone derivatives and a use thereof, more precisely to the novel rotenone derivatives represented by the following formula 1 and a method for the prevention and treatment of obesity using the same.

[Formula 1]

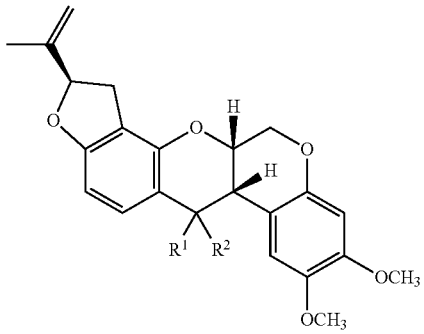

(In formula 1, $R^1$ and $R^2$ are as defined in this description).

BACKGROUND

Obesity originates with the unbalance between energy intake and energy consumption, which has been considered as one of the major causes of health problems. Obesity is closely related to various pathological disorders such as hypertension, hyperlipidemia, arteriosclerosis, degenerative arthritis, type II diabetes, and coronary heart disease. The interaction of natural factors and genetic factors is also a cause of obesity. The treatment method of obesity is categorized according to their different mechanisms like the inhibition of lipase, the inhibition of energy intake, the stimulation of energy consumption, the inhibition of adipocyte differentiation, and the regulation of fat metabolism. A new strategy is recently applied to inhibit pancreatic lipase which is the major reason of excessive calorie to inhibit the absorption of neutral fat (triglyceride) included in food. Pancreatic lipase has been well known as a key enzyme to play an important role in neutral fat (triglyceride) absorption. This enzyme is secreted in pancreas and hydrolyzes neutral fat to glycerol and fatty acid. Orlistat, one of anti-obesity agents, is a potential pancreatic lipase inhibitor obtained naturally from *Streptomyces Toxytricini*, which is clinically utilized for the treatment of obesity by reducing energy intake during meal time. Obesity is defined by the increase in the number and size of adipocytes differentiated from 3T3-L1 preadipocytes. Therefore, the suppression of lipase, and the regulation of fat absorption and accumulation induced by adipocyte differentiation are considered as important factors for the development of anti-obesity agents.

Rotenoids belong to legumes, which have been well known as isoflavonoid generated in Derris, Lonchocarpus, and Tephrosia. These metabolites contain tetrahydrochromeno[3,4b]chromene ring core structure formed by modification of each member. Rotenoids have a wide variety of biological characteristics including potential anti-bacterial, anti-malaria, anti-cancer, and anti-microbial activity, etc. Recent reports proved that rotenone showed potential anti-cancer activity in some cancer cell lines by interacting with microtubules. The above founding opened the possibility for rotenone as an anti-cancer agent candidate, which is drawing our attention. Various attempts have also been made to provide novel and usable derivatives via structural change by chemical synthesis. In those studies, however, rotenone and its derivatives were unnoticed as starting materials for biotransformation. In the meantime, gamma-irradiation was proved in many previous studies to be an effective method to increase bioactivity and induce structural change of natural substances. However, it is still very limited in study of transformation of secondary metabolites having different natural basic structures by irradiation.

The present inventors studied and confirmed that the novel rotenone derivatives isolated and identified by gamma-irradiation had no cytotoxicity but had excellent pancreatic lipase inhibiting activity and adipocyte differentiation inhibiting activity, compared with the mother compound. Based on the above confirmation, the present inventors further completed this invention by proving that the novel rotenone derivatives, thereby, could be effectively used for the prevention and treatment of obesity.

SUMMARY OF THE INVENTION

It is an object of the present invention to provide a novel rotenone derivative.

It is another object of the present invention to provide a preparation method of the said novel rotenone derivative.

It is also an object of the present invention to provide a prevention method or a treatment method for obesity using the novel rotenone derivative.

It is further an object of the present invention to provide a use of the novel rotenone derivative for the prevention or treatment of obesity.

To achieve above objects, the present invention provides the novel rotenone derivative represented by the following formula 1:

[Formula 1]

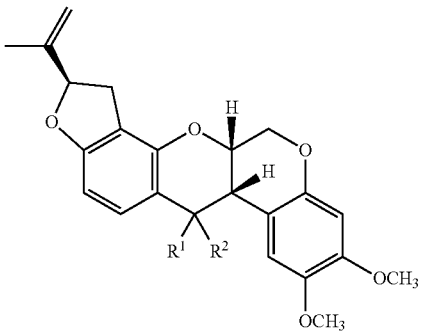

(In formula 1, $R^1$ and $R^2$ are as defined in this description).

The present invention also provides a preparation method of the novel rotenone derivative represented by formula 1.

The present invention also provides a pharmaceutical composition for the prevention and treatment of obesity comprising the novel rotenone derivative represented by formula 1 as an active ingredient.

The present invention also provides a composition for health functional food for the prevention and improvement of obesity comprising the novel rotenone derivative represented by formula 1 as an active ingredient.

The present invention also provides a treatment method for obesity containing the step of administering a pharmaceutically effective dose of the novel rotenone derivative represented by formula 1 to a subject having obesity.

The present invention also provides a prevention method for obesity containing the step of administering a pharmaceutically effective dose of the novel rotenone derivative represented by formula 1 to a subject.

The present invention also provides the novel rotenone derivative represented by formula 1 for the use as a pharmaceutical composition for the prevention and treatment of obesity.

The present invention also provides the novel rotenone derivative represented by formula 1 for the use as a composition for health functional food for the prevention and improvement of obesity.

The novel rotenone derivative of the present invention has no toxicity in human, and significantly inhibits pancreatic lipase activity and preadipocyte differentiation, so that it can be effectively used as an active ingredient of a composition for the prevention and treatment of obesity.

BRIEF DESCRIPTION OF THE DRAWINGS

The application of the preferred embodiments of the present invention is best understood with reference to the accompanying drawings, wherein:

FIG. 1 is a diagram illustrating the inhibitory effect of rotenoisin A and B, the novel rotenone derivatives, on adipocyte differentiation:

Control: positive control;
Rotenone(1): rotenone;
Rotenoisin A(2): the novel rotenoisin A of the present invention; and
Rotenoisin B(3): the novel rotenoisin B of the present invention.

DETAILED DESCRIPTION

Hereinafter, the present invention is described in detail.

The present invention provides the novel rotenone derivative represented by the following formula 1:

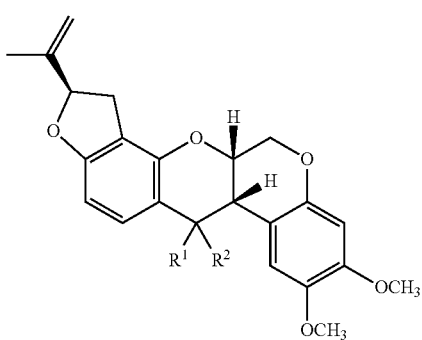

[Formula 1]

In formula 1,
$R^1$ is hydrogen, oxygen, or $C_{1-6}$ straight or branched alkyl,
$R^2$ is hydrogen, or $C_{1-6}$ straight or branched alkyl,
herein, $R^1$ and $R^2$ can be linked each other by ring and this ring can be substituted by —OH or $C_{1-5}$ straight or branched alkyl, and this ring can also form 3-6 membered heterocycle including one or more hetero atoms selected from the group consisting of N, O, and S with neighboring carbon atoms.

Preferably, $R^1$ is oxygen, or $C_{1-3}$ straight or branched alkyl,
$R^2$ is $C_{1-4}$ straight or branched alkyl,
herein, $R^1$ and $R^2$ can be linked each other by ring and this ring can be substituted by —OH, and this ring can also form 3-5 membered heterocycle including one or more hetero atoms selected from the group consisting of N, O, and S with neighboring carbon atoms.

More preferably, $R^1$ is oxygen,
$R^2$ is $C_{1-4}$ straight or branched alkyl,
herein, $R^1$ and $R^2$ can be linked each other by ring and this ring can be substituted by —OH, and this ring can also form 3 membered heterocycle including one or more hetero atoms selected from the group consisting of N, O, and S with neighboring carbon atoms.

The novel rotenone derivative is represented by formula 2 or formula 3.

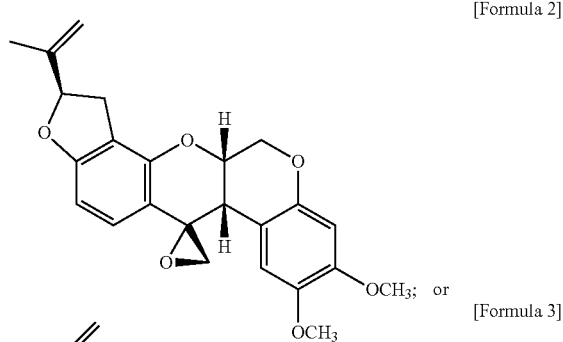

[Formula 2]

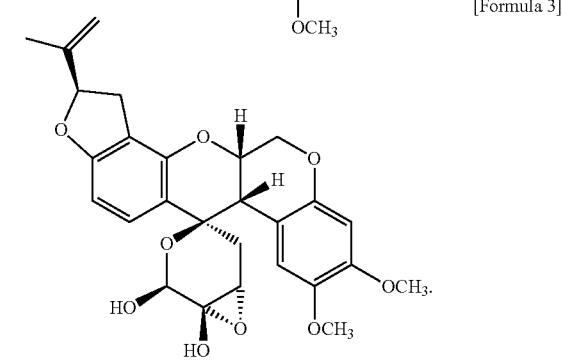

[Formula 3]

The present invention not only includes rotenoisin A and B but also includes the pharmaceutically acceptable salts thereof, every possible solvates, hydrates, racemates, or stereoisomers constructed from the same.

The rotenoisin A and B of the present invention can be used as the form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, or phosphorous acid; or non-toxic organic acids such as aliphatic mono/di-carboxylate, phenyl-substituted alkanoate, hydroxy alkanoate/alkanedioate, aromatic acids, aliphatic and aromatic sulfonic acids. The pharmaceutically non-toxic salt is exemplified by sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maliate, butin-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, or mandelate.

The acid addition salt in this invention can be prepared by the conventional method known to those in the art. For example, one of the rotenoisin A and B of the present invention is dissolved in excessive acid aqueous solution, followed by salt precipitation using water-miscible organic solvent such as methanol, ethanol, acetone, or acetonitrile.

Equal amount of the rotenoisin A and B of the present invention and acid or alcohol in water are heated, followed by drying the mixture to give acid addition salt or suction-filtering the precipitated salt to give the same.

A pharmaceutically acceptable metal salt can be prepared by using base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal with proper silver salt (ex; silver nitrate).

The rotenone derivative of the present invention is preferably prepared by the following steps, but not always limited thereto:

1) irradiating rotenone; and
2) performing column chromatography with the irradiated rotenone of step 1) using chloroform/methanol as solvents, followed by separation and purification of the resultant compound.

The rotenone of step 1) is preferably represented by the following formula 4, but not always limited hereto:

[Formula 4]

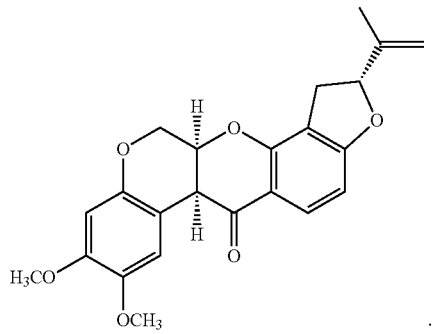

The radiation of step 1) is preferably selected from the group consisting of gamma ray, electron beam, UV, and X ray, and gamma ray is more preferred, but not always limited thereto.

The gamma ray used for irradiation herein is preferably the one emitted from such radioisotope as Co-60, Kr-85, Sr-90, or Cs-137, and gamma ray emitted from Co-60 is more preferred, but not always limited thereto. At this time, the radiation dose is preferably 1μ20 kGy, and more preferably 5~15 kGy, and most preferably 10 kGy. If the radiation dose is less than 1 kGy, reaction is not properly induced. On the other hand, if the radiation dose is over 20 kGy, irradiation costs will rise because of the unnecessary excessive radiation and there might be a risk of compound degradation.

In a preferred embodiment of the present invention, rotenone was irradiated with gamma ray and the irradiated reactant proceeded to column chromatography. As a result, rotenone derivative 1 and rotenone derivative 2, respectively represented by formula 2 and formula 3, were isolated.

To analyze the structure of the isolated compound, nuclear magnetic resonance (NMR) and mass spectrometry were performed. As a result, the rotenone derivative 1 represented by formula 2 was identified to be the novel rotenoisin A, and the rotenone derivative 2 represented by formula 3 was identified to be the novel rotenoisin B (see Table 1).

The present invention also provides a pharmaceutical composition for the prevention and treatment of obesity comprising the novel rotenone derivative represented by formula 1 as an active ingredient.

The present invention also provides a treatment method for obesity containing the step of administering a pharmaceutically effective dose of the novel rotenone derivative represented by formula 1 to a subject having obesity.

The present invention also provides a prevention method for obesity containing the step of administering a pharmaceutically effective dose of the novel rotenone derivative represented by formula 1 to a subject.

The present invention also provides the novel rotenone derivative represented by formula 1 for the use as a pharmaceutical composition for the prevention and treatment of obesity.

The novel rotenone derivative herein is preferably the rotenoisin A represented by formula 2 or the rotenoisin B represented by formula 3, but not always limited thereto.

In a preferred embodiment of the present invention, the present inventors measured pancreatic lipase inhibiting activity of the novel rotenoisin A and B in order to investigate the obesity treating effect of the novel rotenoisin A and B. As a result, the rotenoisin A and B of the present invention demonstrated greater pancreatic lipase inhibiting activity than the conventional rotenone. In particular, $IC_{50}$ (the concentration showing 50% survival rate) of the rotenoisin A was 6.3±0.3 μM, indicating excellent inhibiting activity (see Table 2).

The present inventors also investigated adipocyte differentiation inhibiting activity of the rotenoisin A and B of the present invention in preadipocyte 3T3-L1 cell line. As a result, the rotenoisin A and B of the present invention demonstrated excellent adipocyte differentiation inhibiting activity in preadipocyte 3T3-L1 cell line. In particular, the differentiation inhibiting activity of the rotenoisin A reached approximately 70% at the concentration of 2 μM.

Therefore, the novel rotenone derivative of the present invention has no toxicity in human and significantly inhibits pancreatic lipase activity and preadipocyte differentiation, so that it can be effectively used as an active ingredient of a pharmaceutical composition for the prevention and treatment of obesity.

The composition of the present invention can be prepared for oral or parenteral administration by mixing with generally used diluents or excipients such as fillers, extenders, binders, wetting agents, disintegrating agents and surfactant.

Solid formulations for oral administration are tablets, pills, powders, granules, capsules, and troches. These solid formulations are prepared by mixing the rotenoisin A and B of the present invention with one or more suitable excipients such as starch, calcium carbonate, sucrose or lactose, or gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations, and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The composition of the present invention is administered by pharmaceutically effective dosage. In this invention, the "pharmaceutically effective dosage" indicates the amount that is enough to treat disease at clinically applicable or reasonable benefit/risk ratio. The effective dosage can be determined by considering disease type, severity of disease, activity of drug, sensitivity to drug, administration time, administration pathway, and excretion rate, duration of treatment, other factors including co-treated drug and other medicinal factors. The composition of the present invention can be co-administered with other treating agents or administered alone. The composition can also be administered together with the conventional treatment agents stepwise or simultaneously, singly or multiply. It is important to administer the composition in a way to give maximum effect with the minimum dosage without side effects with considering all the factors mentioned above, which can be determined easily by those in the art.

Particularly, the effective dosage of the rotenoisin A and B of the present invention can be varied from age, gender, and weight of a patient. In general, the effective dosage is 0.1 mg~100 mg/kg, preferably 0.5 mg~10 mg/kg, which is administered every day or every other day, once a day or 3 times a day. However, the dosage can be increased or decreased according to the administration pathway, severity of obesity, gender, weight, age, etc, so the said dosage cannot limit the scope of the present invention in any way.

The present invention also provides a composition for health functional food for the prevention and improvement of obesity comprising the novel rotenone derivative represented by formula 1 as an active ingredient.

The present invention also provides a improvement method for obesity containing the step of administering a pharmaceutically effective dose of the novel rotenone derivative represented by formula 1 to a subject.

The present invention also provides the novel rotenone derivative represented by formula 1 for the use as a composition for health functional food for the prevention and improvement of obesity.

The novel rotenone derivative herein is preferably the rotenoisin A represented by formula 2 or the rotenoisin B represented by formula 3, but not always limited thereto.

The rotenoisin A and B of the present invention has no toxicity in human, and significantly inhibits pancreatic lipase activity and preadipocyte differentiation, so they can be effectively used as an active ingredient of a composition for health functional food for the prevention and improvement of obesity.

Food to which the novel rotenoisin A and B of the present invention are added is not limited. For example, the novel rotenoisin A and B of the present invention can be added to drinks, meat, sausage, bread, biscuits, rice cake, chocolate, candies, snacks, cookies, pizza, ramyun, other noodles, gums, dairy products including ice cream, soups, beverages, alcohol drinks and vitamin complex, etc, and in wide sense, almost every food applicable in the production of health food can be included.

The novel rotenoisin A and B of the present invention can be added as it is or as mixed with other food components according to the conventional method. The mixing ratio of active ingredients can be regulated according to the purpose of use (prevention or improvement). In general, to produce health food or beverages, the novel rotenoisin A and B of the present invention are added preferably by 0.1~90 weight part of the total weight of food. However, if long term administration is required for health and hygiene or regulating health condition, the content can be lower than the above but higher content can be accepted as well since the novel rotenoisin A and B of the present invention have been proved to be very safe.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~10 g in 100 mL of the composition.

In addition to the ingredients mentioned above, the composition of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.1~20 weight part per 100 weight part of the rotenoisin A and B of the present invention.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Rotenone Derivative by Using Gamma Ray

To prepare the novel rotenone derivative from rotenone, rotenone (Sigma Co.) was dissolved in methanol, followed by irradiation.

Particularly, irradiation was performed at room temperature by using Co-60 radiation irradiator (point source AECL, IR-79, MDS Nordion International Co. Ltd, Ottawa, ON, Canada) in Future Nuclear Energy System Research Institute, Korea Atomic Energy Research Institute. Radiation dose of gamma ray was approximately 10 kGy/hour at 320 kCi of a sample. Radiation dose was measured by using 5 mm alanine dosimeter (Brukerinstruments, Rheinstetten, Germany). The dosimeter was corrected with international standard set by International Atomic Energy Agency (Vienna, Austria). 0.5 g of rotenone was dissolved in 200 mL of methanol. The rotenone solution was distributed in vials, which was irradiated at total absorbed dose of 50 kGy. The methanol solution irradiated with gamma ray was dried right away to eliminate solvent and then freeze-dried for preservation.

Example 2

Isolation and Purification of Rotenone Derivative

To isolate and purify rotenone derivative from the reactant obtained in <Example 1>, silica-gel column chromatography and high performance liquid chromatography (HPLC) were performed.

Particularly, the reactant obtained in <Example 1> proceeded to silica-gel column chromatography using chloroform-methanol ($CHCH_3$-MeOH) as a solvent, and as a result the rotenone derivative 1 represented by formula 2 (129.1 mg, tR 4.5 MIN) and the rotenone derivative 2 represented by formula 3 (7.1 mg, tR 4.5 MIN) were obtained, followed by HPLC.

The said rotenone derivative 1 was named rotenoisin A, and the rotenone derivative 2 was named rotenoisin B.

[Formula 2]

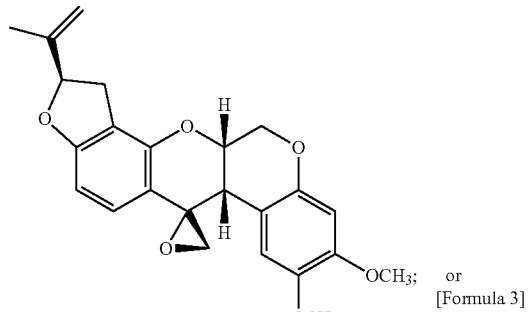

or

[Formula 3]

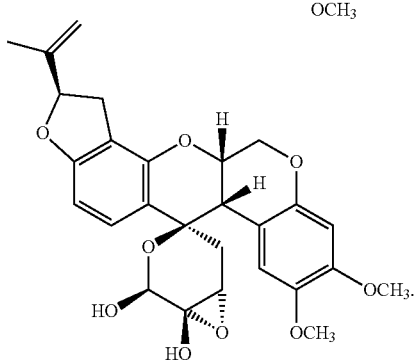

HPLC was performed with YMC-Park ODS A-302 column (4.6 mm id, ×150 mm; YMC Co., Ltd) and 1% formic acid was mixed with acetonitrile at the ratio of 1:1, which was used as a moving phase at the flow rate of 1 mL/min. Column temperature was set at 40° C., and analysis was performed at 280 mm of UV wavelength.

To analyze the structures of the rotenoisin A and B purified by HPLC above, RFAB-MS (Micro Mass Auto Spec OA-TOF spectrometer, Tokyo, Japan) and optical activity (JASCO DIP-4 digital polarimeter, Tokyo, Japan) were measured. As a result, the molecular weight of the rotenoisin A and B was respectively m/z 409.1650 [M+H$^+$](calcd. for $C_{24}H_{24}O_6$: 408.16) and m/z 497.1844 [M+H$^+$] (calcd. for $C_{27}H_{28}O_9$: 496.17). The optical activity of the rotenoisin A and B was respectively $[\alpha]^{20}_D = -95.0°$ and $[\alpha]^{20}_D = -13.0°$.

$^1$H NMR and $^{13}$C NMR of the purified rotenoisin A and B were measured and the results are shown in Table 1.

TABLE 1

$^1$H NMR and $^{13}$C NMR results of rotenoisin A and B [a]

| | rotenoisin A | | rotenoisin B | |
|---|---|---|---|---|
| Site | $\delta_H$(J in Hz)[b] | $\delta_C$, mult | $\delta_H$(J in Hz)[b] | $\delta_C$, mult |
| 1 | 7.42(s) | 116.7 | 6.92(s) | 114.1 |
| 1a | — | 111.8 | — | 111.7 |
| 2 | — | 143.9 | — | 144.0 |
| 3 | — | 150.4 | — | 149.0 |
| 4 | 6.36(s) | 101.6 | 6.32(s) | 102.4 |
| 4a | — | 151.2 | — | 150.1 |
| 6α | 4.13(d, 10.8) | 67.4 | 4.03(d, 11.4) | 69.4 |
| 6β | 4.51(dd, 10.8, 1.8) | | 4.42(dd, 11.4, 2.4) | |
| 6a | 4.81(d, 1.8) | 71.6 | 5.06(m) | 70.4 |
| 7a | — | 151.7 | — | 151.3 |
| 8 | — | 113.4 | — | 114.1 |
| 9 | — | 162.2 | — | 162.1 |
| 10 | 6.31(d, 8.4) | 102.8 | 6.20(d, 8.4) | 101.0 |
| 11 | 7.21(d, 8.4) | 127.6 | 7.65(d, 8.4) | 130.7 |
| 11a | — | 117.9 | — | 113.9 |
| 12 | — | 73.7 | — | 75.4 |
| 12a | 3.62(brs) | 37.5 | 3.72(d, 4.8) | 40.6 |
| 14a | 3.94(d, 11.4) | 68.8 | 5.75(s) | 92.5 |
| 14b | 3.64(d, 11.4) | | | |
| 15 | | | — | 92.6 |
| 16 | | | 3.65(m) | 61.7 |
| 17a | | | 4.32(dt, 3.0, 12.0) | 59.1 |
| 17b | | | 3.46(m) | |
| 2' | 5.14(dd, 9.6, 8.4) | 87.7 | 5.13(m) | 87.7 |
| 3'α | 3.22(dd, 15.6, 9.6) | 33.0 | 3.20(m) | 33.0 |
| 3'β | 2.85(dd, 15.6, 8.4) | | 2.86(dd, 16.2, 7.8) | |
| 4' | — | 146.0 | — | 146.0 |
| 5' | 4.80(m) | 111.9 | 5.02(brs) | 111.8 |
| | | | 4.85(d, 6.0) | |
| 6' | 1.72(s) | 17.2 | 1.73 | 17.2 |
| $OCH_3$-2 | 3.71(s) | 57.3 | 3.67(s) | 57.4 |
| $OCH_3$-3 | 3.73(s) | 56.2 | 3.70(s) | 56.1 |

[a] $^1$H MNR was measured at 600 MHz and $^{13}$C NMR was measured at 150 MHz; CD$_3$OD and TMS were obtained according to the international standard. The measurement was performed based on HMQC and HMBC spectra.
[b] J value was presented in bracket.

Experimental Example 1

Measurement of Pancreatic Lipase Inhibiting Activity

To investigate obesity treating effect of the novel rotenoisin A and B, each represented by formula 2 and formula 3 isolated and purified in <Example 2>, pancreatic lipase inhibiting activity of the same was measured.

Particularly, pancreatic lipase inhibiting activity was measured by the conventional method known to those in the art (Kim, J. H.; Kim, H. J.; Park, H. W.; Youn, S. H.; Choi, D. Y.; Shin, C. S. *FEMS Microbiol. Lett.* 2007, 276, 93.). To prepare the enzyme buffer, 30 mL (10 units) of pig pancreatic lipase solution (Sigma, St. Louis, Mo.) and 1 mM EDTA (pH 6.8) were mixed with 10 mM MOPS (morpholinepropanesulphonic acid), which was added to 850 mL of tris buffer (100 mM Tris-HCl and 5 mM $CaCl_2$, pH 7.0). Then, 100 mL of the rotenoisin A or B of the present invention was mixed with the prepared enzyme buffer at the experimental concentration. As the positive control, 880 mL of Orlistat (Roche, Basel, Switzerland) was mixed with the enzyme buffer. 20 mL of substrate solution containing 20 mM p-nitrophenylbutyrate dissolved in dimethyl formaide was added to the enzyme buffer, followed by culture for 15 minutes at 37° C. that was the temperature adequate for enzyme reaction. Pancreatic lipase activity was measured by measuring the hydrolysis of p-nitrophenylbutyrate into p-nitrophenol using an ELISA reader (Infinite F200; Tecan Austria GmBH, Grodig, Austria). To confirm the inhibition of lipase activity, pig pancreatic lipase was cultured with the rotenoisin A or B of the present invention and the reduction of optical density (OD) rate was investigated.

As a result, as shown in Table 2, the rotenoisin A and B of the present invention demonstrated significantly higher pancreatic lipase inhibiting activity than the conventional rotenone. In particular, rotenoisin A showed excellent inhibiting activity with demonstrating $IC_{50}$ to be 6.3±0.3 μM (Table 2).

TABLE 2

Pancreatic lipase inhibiting activity of rotenone, rotenoisin, and rotenoisin A/B irradiated with gamma ray

| Compound | $IC_{50}$ value (uM)[a] |
| --- | --- |
| Gamma-irradiated rotenone | 31.2 ± 1.3[b] |
| rotenone | >500 |
| rotenoisin A | 6.3 ± 0.3 |
| rotenoisin B | 28.4 ± 1.2 |
| Orlistat[c] | 0.6 ± 0.2 |

[a]Every experiment was performed in triplicate.
[b]$IC_{50}$ value was presented as ug/mL.
[c]positive control.

Experimental Example 2

Inhibition of Differentiation of 3T3-L1 Preadipocyte to Adipocyte

To investigate inhibition effect on adipocyte differentiation in 3T3-L1 preadipocytes, mouse embryo fibroblasts were cultured in DMEM supplemented with 10% FBS to confluency. Two days later (Day 0), the cells were stimulated for the differentiation in DMEM, the differentiation medium supplemented with 10% FBS, 0.5 mM 3-isobutyl-1-methyl-xanthine, 1 mM insulin, and 1 mM dexamethasone (Day 2). For the next 6 days, the cells were cultured in DMEM supplemented with 10% FBS and 2 mM insulin (Day 8), followed by further culture in DMEM supplemented with 10% FBS for 4 more days (Day 8). Every medium was added with 100 IU/ml of penicillin and 100 mg/mL of streptomycin. The cells were cultured in the presence of 95% air and 5% $CO_2$. During the whole culture period (Day 0~Day 8), the treatment of the rotenoisin A and B (2, 0.2, 0.02 uM) of the present invention was performed by the conventional method known to those in the art (Liu, Q.; Shin, E.; Ahn, M. J.; Hwang, B. Y.; Lee, M. K. Nat. Prod. Sci. 2011, 17, 212.) with slight modification. Then, oil red O staining was performed.

Particularly, intracellular fat lump was stained with oil red O. 8 days after the induction of cell differentiation, the cells were washed with FBS twice, followed by fixing in 10% formalin for 1 hour at room temperature. The cells were washed with 60% isopropyl alcohol once, followed by staining with diluted oil red O solution (prepared by mixing isopropyl alcohol containing 0.6% oil red O and water at the ratio of 3:2) for 1 hour. Then, the cells were washed with water twice, followed by visualization. For quantitative analysis, oil red O was dissolved with isopropyl alcohol, followed by measuring $OD_{500}$ using an ELISA reader.

As a result, the rotenoisin A and B of the present invention significantly inhibited the differentiation of 3T3-L1 preadipocytes. In particular, rotenoisin A had excellent differentiation inhibiting activity, which was approximately 70% inhibition at the concentration of 2 μM (FIG. 2).

Manufacturing Example 1

Preparation of Pharmaceutical Formulations

<1-1> Preparation of Powders

| Rotenoisin A or B of the present invention | 2 g |
| --- | --- |
| Lactose | 1 g |

Powders were prepared by mixing all the above components, which were filled in airtight packs according to the conventional method for preparing powders.

<1-2> Preparation of Tablets

| Rotenoisin A or B of the present invention | 100 mg |
| --- | --- |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| Rotenoisin A or B of the present invention | 100 mg |
| --- | --- |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| Rotenoisin A or B of the present invention | 1 g |
| --- | --- |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| Rotenoisin A or B of the present invention | 150 mg |
| --- | --- |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Health Food

| | |
|---|---|
| Rotenoisin A or B of the present invention | 10 g |
| Vitamin complex | proper amount |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating obesity comprising:
   administering a pharmaceutically effective dose of a rotenone derivative represented by formula 2 or formula 3 to a subject having obesity,

[Formula 2]

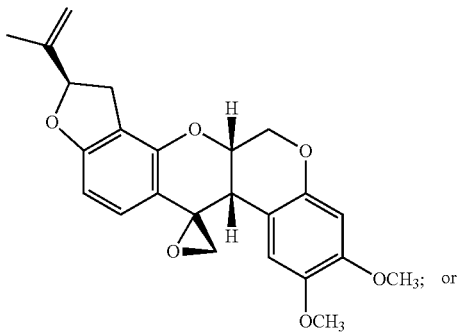

[Formula 3]

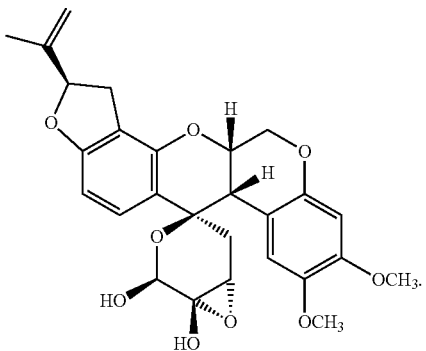

2. The method for treating obesity according to claim 1, further comprising administering a carrier, diluent, or excipient with said rotenone derivative.

* * * * *